(12) United States Patent
Roe et al.

(10) Patent No.: US 9,179,872 B2
(45) Date of Patent: Nov. 10, 2015

(54) LANCETS FOR BODILY FLUID SAMPLING SUPPLIED ON A TAPE

(71) Applicant: Roche Diagnostics Operations, Inc., Indianapolis, IN (US)

(72) Inventors: Steven N. Roe, San Mateo, CA (US); Charles C. Raney, Camdenton, MO (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/062,198

(22) Filed: Oct. 24, 2013

(65) Prior Publication Data

US 2014/0052025 A1 Feb. 20, 2014

Related U.S. Application Data

(62) Division of application No. 10/836,578, filed on Apr. 30, 2004, now Pat. No. 8,591,436.

(51) Int. Cl.
*A61B 5/00* (2006.01)
*B65D 81/00* (2006.01)
(Continued)

(52) U.S. Cl.
CPC ........... *A61B 5/15169* (2013.01); *A61B 5/1411* (2013.01); *A61B 5/157* (2013.01);
(Continued)

(58) Field of Classification Search
CPC ............. A61B 5/1451; A61B 5/14514; A61B 5/1411; A61B 5/15003; A61B 5/15103; A61B 5/15113; A61B 5/00
USPC ........... 600/583, 573, 576, 577; 606/181–183
See application file for complete search history.

(56) References Cited

U.S. PATENT DOCUMENTS 2,989,212 A 6/1961 Ekenstam et al.
3,039,652 A 6/1962 Ekenstam et al.
(Continued)

FOREIGN PATENT DOCUMENTS

DE 28 03 345 6/1979
DE 198 19 407 A1 11/1999
(Continued)

OTHER PUBLICATIONS

Priebs, Hendrik. "Test Strip Container for Measurement Devices which Operate with a One-Way Test Strip", Nov. 11, 1999. Certified translation of DE 19819407 produced Feb. 2011 by Schreiber Translations, Inc.
(Continued)

*Primary Examiner* — Rene Towa
*Assistant Examiner* — May Abouelela
(74) *Attorney, Agent, or Firm* — Woodard, Emhardt, Moriarty, McNett & Henry LLP

(57) ABSTRACT

A supply of lancets for a multi-use lancing device are carried by a tape and sequentially brought from a storage position to an activating position by advancing the tape around a bend. In the lancets' activating position they extend from the tape such that their sharp tips are available for lancing tissue. The carrying tape can be arranged in reel-to-reel format in a housing having a lancing opening. The lancets can be integral with the tape and activated to move the lancet through the lancing opening by moving the tape along its tape path or by translating a dedicated service loop of the tape. The lancets can also be independent from the tape and activated through the lancing opening by a separate lancing actuator. A test media can be included on the carrying tape and the housing can contain a sensor to yield an integrated lancing and testing device.

15 Claims, 5 Drawing Sheets

(51) Int. Cl.
- *A61B 17/32* (2006.01)
- *A61B 5/151* (2006.01)
- *A61B 5/15* (2006.01)
- *A61B 5/157* (2006.01)
- *A61B 5/145* (2006.01)

(52) U.S. Cl.
CPC ......... *A61B5/15146* (2013.01); *A61B 5/15155* (2013.01); *A61B 5/15173* (2013.01); *A61B 5/150419* (2013.01); *A61B 5/14532* (2013.01); *Y10T 436/110833* (2015.01)

(56) References Cited

U.S. PATENT DOCUMENTS

| | | | |
|---|---|---|---|
| 3,526,480 A | 9/1970 | Findl at al. | |
| 3,620,678 A | 11/1971 | Guigan et al. | |
| 3,786,510 A | 1/1974 | Hodges | |
| 3,835,992 A | 9/1974 | Adams, IV | |
| 4,123,840 A | 11/1978 | Rumer, Jr. | |
| 4,218,421 A | 8/1980 | Mack, Jr. et al. | |
| 4,328,184 A | 5/1982 | Kondo | |
| 4,790,979 A | 12/1988 | Terminiello et al. | |
| 4,883,642 A | 11/1989 | Bisconte | |
| 4,924,879 A | 5/1990 | O'Brien | |
| 4,969,738 A | 11/1990 | Mann | |
| 4,995,402 A | 2/1991 | Smith et al. | |
| 5,035,704 A | 7/1991 | Lambert et al. | |
| 5,047,044 A | 9/1991 | Smith et al. | |
| 5,077,010 A | 12/1991 | Ishizaka et al. | |
| 5,096,828 A | 3/1992 | Ishizaka et al. | |
| 5,178,835 A | 1/1993 | Uekusa et al. | |
| 5,228,972 A | 7/1993 | Osaka et al. | |
| 5,231,993 A | 8/1993 | Haber et al. | |
| 5,361,901 A | 11/1994 | Schenz et al. | |
| 5,679,311 A | 10/1997 | Harttig et al. | |
| 5,686,829 A | 11/1997 | Girault | |
| RE35,803 E | 5/1998 | Lange et al. | |
| 5,776,157 A | 7/1998 | Thorne et al. | |
| 5,857,983 A | 1/1999 | Douglas et al. | |
| 5,879,311 A | 3/1999 | Duchon et al. | |
| 5,887,778 A | 3/1999 | Maurer et al. | |
| 5,964,718 A | 10/1999 | Duchon et al. | |
| 5,971,941 A | 10/1999 | Simons et al. | |
| 5,997,817 A | 12/1999 | Crismore et al. | |
| 6,036,924 A | 3/2000 | Simons et al. | |
| 6,071,294 A | 6/2000 | Simons et al. | |
| 6,102,927 A | 8/2000 | Wright | |
| 6,183,489 B1 | 2/2001 | Douglas et al. | |
| 6,332,871 B1 | 12/2001 | Douglas et al. | |
| 6,334,856 B1 | 1/2002 | Allen et al. | |
| 6,472,220 B1 | 10/2002 | Simons et al. | |
| 6,488,891 B2 | 12/2002 | Mason et al. | |
| 6,540,675 B2 | 4/2003 | Aceti et al. | |
| 6,887,709 B2 | 5/2005 | Leong | |
| 6,988,996 B2 * | 1/2006 | Roe et al. | 600/584 |
| 7,862,519 B1 * | 1/2011 | Ward et al. | 600/583 |
| 7,909,776 B2 * | 3/2011 | Roe et al. | 600/583 |
| 2002/0006355 A1 | 1/2002 | Whitson | |
| 2002/0020688 A1 | 2/2002 | Sherman et al. | |
| 2002/0050573 A1 | 5/2002 | Suguro et al. | |
| 2002/0052618 A1 | 5/2002 | Haar et al. | |
| 2002/0076349 A1 | 6/2002 | Aitken et al. | |
| 2002/0076357 A1 | 6/2002 | Hahs et al. | |
| 2002/0087056 A1 | 7/2002 | Aceti et al. | |
| 2002/0120216 A1 * | 8/2002 | Fritz et al. | 600/583 |
| 2002/0188224 A1 * | 12/2002 | Roe et al. | 600/584 |
| 2003/0019901 A1 | 1/2003 | Kim | |
| 2003/0050573 A1 * | 3/2003 | Kuhr et al. | 600/567 |
| 2003/0083685 A1 | 5/2003 | Freeman et al. | |
| 2003/0083686 A1 * | 5/2003 | Freeman et al. | 606/181 |
| 2003/0153939 A1 | 8/2003 | Fritz et al. | |
| 2003/0171699 A1 | 9/2003 | Brenneman | |
| 2003/0191415 A1 | 10/2003 | Moerman et al. | |
| 2003/0199789 A1 | 10/2003 | Boecker et al. | |
| 2003/0199895 A1 | 10/2003 | Boecker et al. | |
| 2003/0199896 A1 | 10/2003 | Boecker et al. | |
| 2003/0199897 A1 | 10/2003 | Boecker et al. | |
| 2003/0199902 A1 * | 10/2003 | Boecker et al. | 606/181 |
| 2003/0199904 A1 | 10/2003 | Boecker et al. | |
| 2003/0211619 A1 * | 11/2003 | Olson et al. | 436/44 |
| 2003/0212344 A1 | 11/2003 | Yuzhakov et al. | |
| 2004/0034318 A1 | 2/2004 | Fritz et al. | |
| 2004/0120848 A1 | 6/2004 | Teodorczyk | |
| 2004/0138688 A1 | 7/2004 | Giraud | |
| 2004/0230216 A1 * | 11/2004 | Levaughn et al. | 606/181 |
| 2005/0021066 A1 | 1/2005 | Kuhr et al. | |
| 2005/0149088 A1 | 7/2005 | Fukuda et al. | |
| 2005/0201897 A1 * | 9/2005 | Zimmer et al. | 422/82.05 |
| 2005/0232815 A1 * | 10/2005 | Ruhl et al. | 422/66 |
| 2005/0245845 A1 | 11/2005 | Roe et al. | |
| 2005/0245954 A1 | 11/2005 | Roe et al. | |
| 2006/0200045 A1 | 9/2006 | Roe | |

FOREIGN PATENT DOCUMENTS

| | | | |
|---|---|---|---|
| DE | 19819407 A1 * | 11/1999 | |
| DE | 198 49 539 A1 | 5/2000 | |
| DE | 198 57 426 A1 | 6/2000 | |
| EP | 0 637 749 A2 | 2/1995 | |
| EP | 0 732 590 | 1/1996 | |
| EP | 1 190 674 | 9/2001 | |
| EP | 1 203 563 A2 | 5/2002 | |
| EP | 1 321 769 A1 | 6/2003 | |
| EP | 1 360 935 A1 | 11/2003 | |
| JP | H01-105157 A1 | 4/1989 | |
| JP | H05-010951 | 1/1993 | |
| JP | H05-045363 | 2/1993 | |
| JP | 2002/103511 | 4/2002 | |
| JP | 2004/000493 A | 1/2004 | |
| JP | 2004/000600 A | 1/2004 | |
| WO | WO 93/09710 A1 | 5/1993 | |
| WO | WO 01/66010 | 9/2001 | |
| WO | WO 02/18940 A2 | 3/2002 | |
| WO | WO 02/36010 | 3/2002 | |
| WO | WO 02/26129 A1 | 4/2002 | |
| WO | WO 03/082092 A1 | 10/2003 | |
| WO | WO 2004/160174 | 7/2004 | |
| WO | WO 2005/104948 A1 | 11/2005 | |
| WO | WO 2007/147494 A2 | 12/2007 | |

OTHER PUBLICATIONS

U.S. Appl. No. 10/836,578 Office Action mailed Aug. 14, 2009.
U.S. Appl. No. 11/105,686 Office Action mailed Sep. 3, 2009.
U.S. Appl. No. 11/105,686 to Roe et al., Non-Final Office Action mailed Jul. 9, 2010.
U.S. Appl. No. 11/537,791 Final Office Action mailed Aug. 13, 2009.
U.S. Appl. No. 11/537,791 to Calasso et al., Office Action mailed Feb. 2, 2010.
U.S. Appl. No. 13/027,337 to Roe et al., Final Office Action mailed Nov. 29, 2012.
U.S. Appl. No. 13/027,337 to Steven N. Roe, Notice of Allowance mailed Aug. 15, 2013.
U.S. Appl. No. 11/070,502, filed Mar. 2, 2005 to Roe.

* cited by examiner

LANCETS FOR BODILY FLUID SAMPLING SUPPLIED ON A TAPE

CROSS-REFERENCE TO RELATED APPLICATION

This application is a divisional of application Ser. No. 10/836,578, filed Apr. 30, 2004, which is hereby incorporated by reference.

BACKGROUND

The present invention generally relates to bodily fluid sampling and more specifically, but not exclusively, concerns bodily fluid sampling devices having a supply of sterile lancets carried by a tape.

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, such as blood and/or interstitial fluid. Such fluids can be tested for a variety of characteristics of the fluid, or analytes contained in the fluid, in order to identify a medical condition, determine therapeutic responses, assess the progress of treatment, and the like.

The testing of bodily fluids begins with obtaining the fluid sample. One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

The other common technique for collecting a blood or other bodily fluid sample is to form an incision in the skin to bring the fluid to the skin surface. According to this technique, a lancet, such as a needle, knife or other cutting instrument, is used to form the incision in the skin. The resulting blood or interstitial fluid specimen may then be collected in a small tube or other container, or placed directly in contact with a test strip or otherwise analyzed. Because lancets are necessarily sharp, lancing devices are typically constructed to protect the lancets when not in use to avoid injuries and contamination.

However, many existing lancing devices are generally designed to hold a single lancet and after lancing require manual replacement of the lancets before performing a subsequent lancing. Particularly where an individual needs to obtain multiple samples per day, it can be inefficient and inconvenient to carry a separate supply of lancets or to use a separate device for each lancing event. A self contained multi-use lancing device could avoid the problems of manually replacing a used lancet, but there are challenges in designing a multi-use lancing device that can safely and reliably handle the lancets yet is compact in design and simple for a lay operator to use and which is also economical to manufacture. Accordingly, there is a need in the art for a multi-use lancing device that meets some or all of these challenges. In one form, the present invention addresses this need and provides a multi-use lancing device that is simple and safe for a lay operator to use and that is cost-effective to manufacture. In other forms the present invention provides other advancements in the art.

SUMMARY

The present invention provides novel systems and techniques for lancing tissue either alone or in combination with testing of the resulting bodily fluid. While the actual nature of the invention covered herein can only be determined with reference to the claims appended hereto, certain aspects of the invention that are characteristic of the embodiments disclosed herein are described briefly as follows.

According to one aspect, the invention provides a novel supply of lancets on a tape.

According to another aspect, the invention provides novel systems and techniques for obtaining bodily fluid samples.

According to still other aspects, novel methods of supplying lancets on a tape and of lancing tissue are disclosed.

These and other aspects are discussed below.

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures forming a part thereof.

DESCRIPTION OF THE ILLUSTRATED EMBODIMENTS

Figure 1:
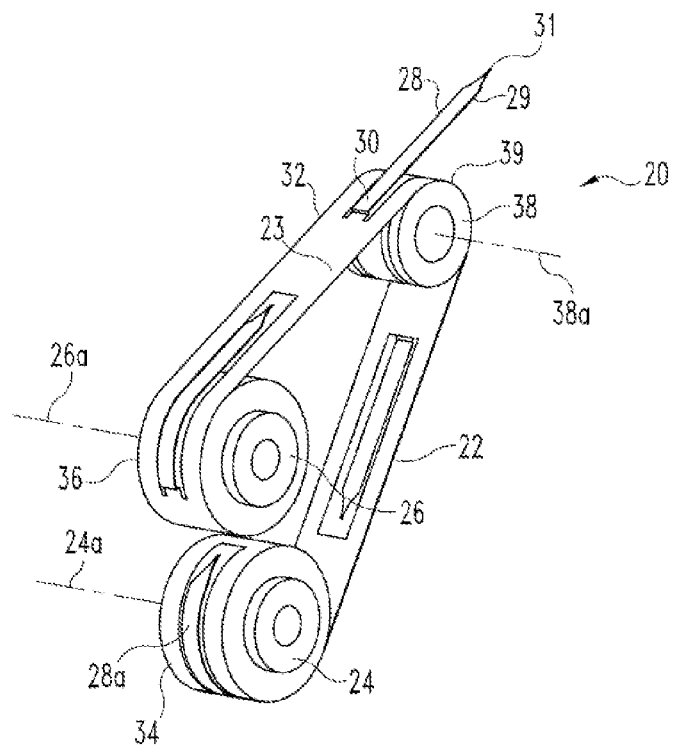
FIG. 1 is a perspective view of a supply of lancets in reel to reel format.

For the purposes of promoting an understanding of the principles of the invention, reference will now be made to the embodiments illustrated in the drawings and specific language will be used to describe the same. It will nevertheless be understood that no limitation of the scope of the invention is hereby intended. Alterations and further modifications in the illustrated devices, and such further applications of the principles of the invention as illustrated herein are contemplated as would normally occur to one skilled in the art to which the invention relates.

In one form, the present invention provides a compact supply of lancets for sampling bodily fluids. The lancets have a non-circular cross section and are arranged on a carrying tape such that the lancets can be sequentially brought from a storage position to an activating position by advancing the tape around a bend. In the activating position, the lancets extend from the tape and their sharp tips are available for lancing tissue, whereas in the storage position the lancets are generally aligned with the carrying tape to facilitate compact storage of the lancets. The carrying tape is contained in a housing defining a lancing opening, and during lancing, the sharp tip of a lancet in the activating position is rapidly advanced and retracted through the lancing opening to pierce adjacent tissue and obtain the bodily fluid sample. After lancing, advancement of the tape brings the used lancet back into a storage position and also positions the next lancet in the activating position to be ready for a subsequent lancing.

As will be described more fully below, there are a variety of mechanisms that can be employed for advancing and retracting the lancets to cause the lancing motion. For example, in certain embodiments the lancets are integral with the tape and rapid movement of the tape results in the lancing motion of the lancet. In one form, the entire tape is moved along its tape path, while in another form only a service loop of the tape is actuated in a lancing motion. In other embodiments, where the lancets are not integral with the tape, a separate actuator can be used to engage the lancets and move them in the lancing motion independent of any movement of the adjacent tape.

Turning now to FIG. 1, a supply of lancets according to one embodiment where the lancets are integral with the tape is depicted. Device 20 includes a carrying tape 22 and a plurality of lancets 28 sequentially positioned along the length of the tape 22. Each of the lancets 28 have a proximal portion 30, a distal portion 29, and a sharp tip 31 at the distal end of their distal portions 29. The length of the tape 22 includes a supply section 34 followed by an activating section 32 followed by a storage section 36. The supply section 34 is wrapped around a supply reel 24, and the storage section 36 is wrapped around a storage reel 26. In the activating section 32, the tape 22 passes around a wheel 38 resulting in a bend 39 in the path of the tape 22.

As mentioned above, in this embodiment the lancets 28 are integral with the tape 32. More specifically, the proximal portions 30 of the lancets 28 are integral with the tape 22 whereas the distal portions 29 are free to extend from the tape 22 when the lancet is in its activating position (described more fully below). This can be accomplished by forming the tape 22 and lancets 28 from the same piece of tape stock by etching, punching, or otherwise removing portions of the tape stock to form the profile of the lancets 28. In the FIG. 1 embodiment, the proximal ends of the lancets are then crimped to cause the main body of the lancets to normally lie slightly offset from but parallel to the plane of the adjacent surface 23 of the tape 32. In other embodiments, the lancets are similarly formed but not crimped, and thus in these embodiments the lancets would normally lie in the plane of the tape surface 32. In still other embodiments, the lancets 28 are independently formed and then made integral with the tape 22, such as by being attached to the tape 22 with a clip, adhesive, or welding.

Both the lancets 28 and the tape 22 are thin and sufficiently deformable to permit the reel-to-reel transfer of the tape 22 carrying the lancets 28 from the supply reel 24 to the storage reel 26. The lancets 28 (and tape 22) are constructed of material having sufficient shape memory or resiliency to allow the lancets 28 to return to a generally linear orientation upon being unwound from the supply reel 24. As a result, when the lancet 22 is positioned adjacent the bend 39 in the tape 22, its sharp tip 31 is spaced from the tape 22 and available for lancing. This position is referred to as the activating position, and as depicted in FIG. 1, lancet 28 is in its activating position. By contrast, lancet 28a is in a different orientation relative to the tape 22, and the orientation of lancet 28a is referred to herein as a storage position.

Figure 2:
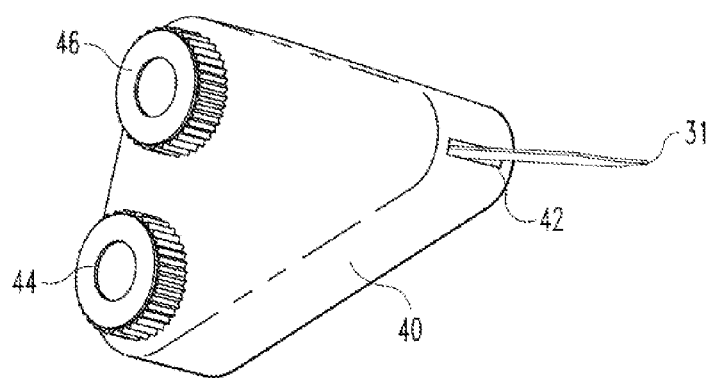
FIG. 2 is a perspective view of a multi-use lancing device utilizing the FIG. 1 lancets.

Referring to FIG. 2, the device 20 is contained in a housing 40 defining a lancing opening 42. The lancing opening 42 receives the tip 31 of a lancet 28 that is in its activating position. The device 20 is configured such that the axes of rotation 24a, 26a, and 38a of the supply reel 24, storage reel 26a and wheel 38, respectively (see FIG. 1), are all generally parallel. A pair of knobs 44 and 46 are operatively coupled to the supply reel 24 and the storage reel 26 respectively for advancing and activating the lancets 28. During operation, knob 46 is used to advance the tape 22 to bring a lancet from the storage reel 24, where it is uncontaminated with the bodily fluid, to its activating position. With the tip 31 positioned towards the lancing opening 42, the tape 22 is reversed via knob 44 to cause the lancet 28 to project out of the lancing opening 42. After use, the tape 22 is again advanced to move the used lancet 28 onto the storage reel 26.

In a preferred form, the movement of the tip 31 through the lancing opening is a rapid back and forth motion generally along the line defining the longitudinal length of the lancet. This is referred to as a lancing motion. The knobs 44 and 46 may each be configured to include a clutch and appropriate spring biasing to provide for this rapid lancing movement by moving the tape 22 rapidly back and forth along its path. As an alternative to achieving the back and forth lancing motion by the back and forth movement of the tape 22 along its tape path, the entire device 20 can be mounted in the housing 40 such that the entire device 20 is translated in a back and forth movement. In a still further embodiment, only a portion of the tape 22 is moved during lancing. An embodiment providing for the lancing motion via relative movement of only a part of the tape 22 is depicted in FIG. 3

Figure 3:
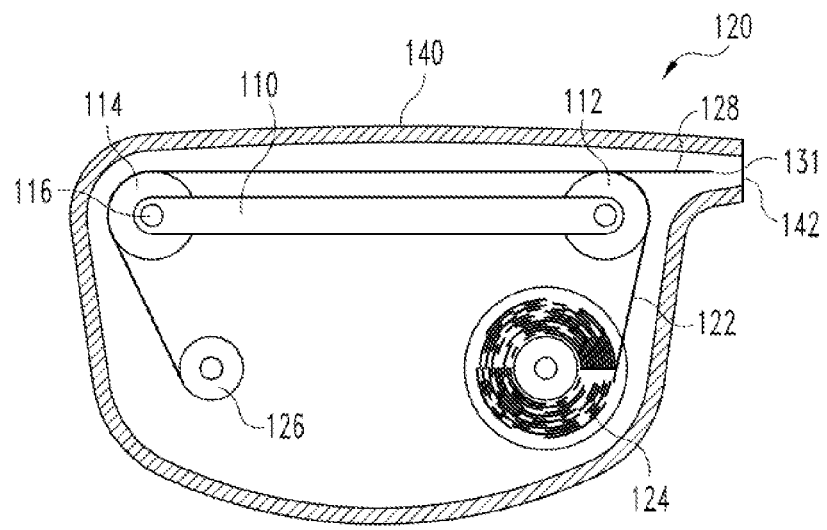
FIG. 3 is a sectional view of a multi-use lancing device according to another embodiment.

The multi-use lancing device 120 of FIG. 3 includes a carrying tape 122 and a plurality of lancets 128 constructed in similar fashion as tape 22 and lancets 28 of the FIG. 1 device. Tape 122 is similarly wrapped around a supply reel 124 and a storage reel 126 and mounted in a housing 140 that has a lancing opening 142. However, unlike the tape 22 of FIG. 1, the activating portion of tape 122 is formed into a service loop that is translatable independently of the remainder of the tape 122.

Figure 4:
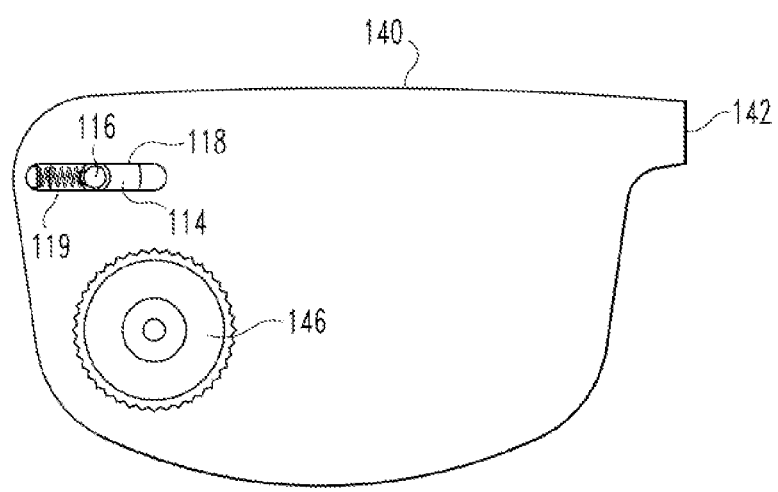
FIG. 4 is a side view of the FIG. 3 multi-use lancing device.

More specifically, the activating portion of tape 122 passes around a pair of wheels 112 and 114 that are freely rotatable but whose longitudinal translation is tied together by tie rod 110. Referring to FIG. 4, the axle 116 of rear wheel 114 is configured to travel in a guiding slot 118 of the housing 140 such that when a lancet 128 is in its activating position (e.g. lancet 128 of FIG. 3), the axle 116 can be pulled to the left of the FIG. 3 view so as to compress spring 119. This compressions cocks the device, and upon release, the spring 119 pushes the axle 116 and the wheels 114 and 112 to the right of the FIG. 3 view. This in turn causes the tip 131 of the lancet 128 to rapidly advance through the lancing opening 142. Recoil of the spring 119 brings the lancet 128 back inside the housing, and then knob 146 is turned to advance the tape 122 onto the storage reel 126 and also to position the next lancet 128 from the supply reel 124 into the activating position. The process may then be repeated for the next lancing.

Figure 5:
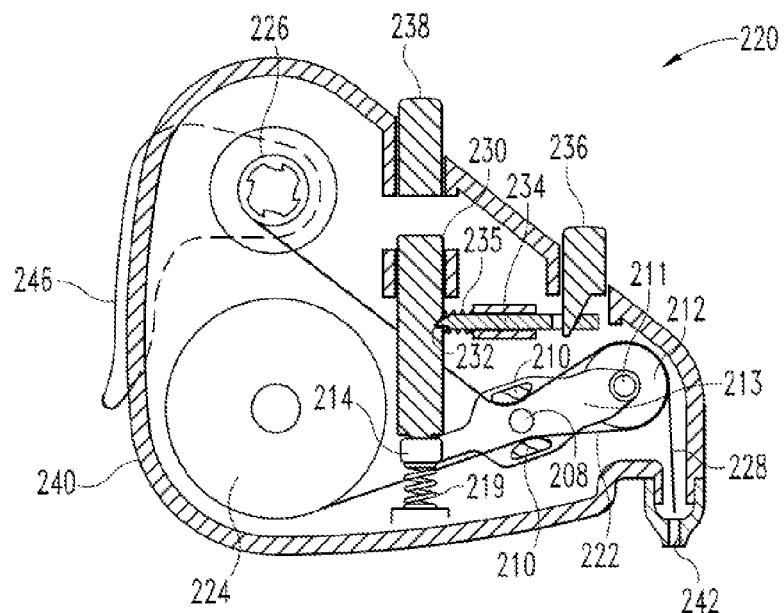
FIG. 5 is a sectional view of a multi-use lancing device according to another embodiment.

A further variation on the use of a service loop is utilized in the device 220 of FIG. 5. The multi-use lancing device 220 includes a supply reel 224 and a storage reel 226 mounted in a housing 240 defining a lancing opening 242. A lever 246 is coupled to the storage reel 226 and is used to advance the tape 222 to position lancet 228 in its activating position adjacent the wheel 212. Axis 211 of wheel 212 is mounted at one end of a pivot arm 213. The pivot arm 213 is configured to pivot about pin 208, and a pair of tape guides 210 are mounted on the arm 213 adjacent the pivot pin 208. The other end of the pivot arm 213 is connected to a coupling 214 between piston 230 and compression spring 219 such that, as viewed in FIG. 5, vertical movement of piston 230 is translated into pivotal motion of the pivot arm 213. The connection between pivot arm 213 and coupling 214 can be a pin-in-slot (not shown) or similar coupling arrangement that would accommodate the arc of the pivot arm 213 relative to the linear motion of piston 230 as the arm 213 pivots about pin 208.

The device 220 is configured for two-button operation. A cocking button 238 serves to drive the piston 230 downward in the FIG. 5 view and compress the spring 219. The compression continues until a recess 232 in the piston 230 reaches a firing pin 234, at which point the firing pin 234, because it is biased by spring 235 toward piston 230, seats into recess 232 and holds the piston 230 in position. This position involves the pivot arm 213 being in the cocked position that is depicted in FIG. 5. When ready for lancing, the fire button 236 is depressed, and a cam surface of the fire button engages a corresponding cam surface on the firing pin to withdraw the pin 234 from the recess 232. This frees the piston 230, and the force of the compression spring 219 drives the piston upward in the FIG. 5 view. This movement in turn raises the coupling 214 end of the pivot arm 213, causing the pivot arm 213 to pivot and thereby advancing the lancet 228 through the opening 242. Relaxation of the spring brings the arm 213 to an intermediate position wherein the lever 246 is activated to advance the now used lancet 228 towards the storage reel 226.

It is to be understood that after lancing, the bodily fluid can be collected and analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Typically, a test system contacts the bodily fluid to be tested with a test media and takes advantage of a reaction between the bodily fluid and a reagent present in the test media. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

While the embodiments of FIGS. 1-5 have been illustrated as stand alone lancing devices for obtaining the bodily fluid sample, it is contemplated that these and other embodiments can be adapted to provide lancing and testing in a single device. One mechanism for accomplishing this is to incorporate a test strip on the lancet carrying tape, to contact the produced bodily fluid with the test strip, and then to analyze the test strip with an incorporated sensor.

Figure 6:
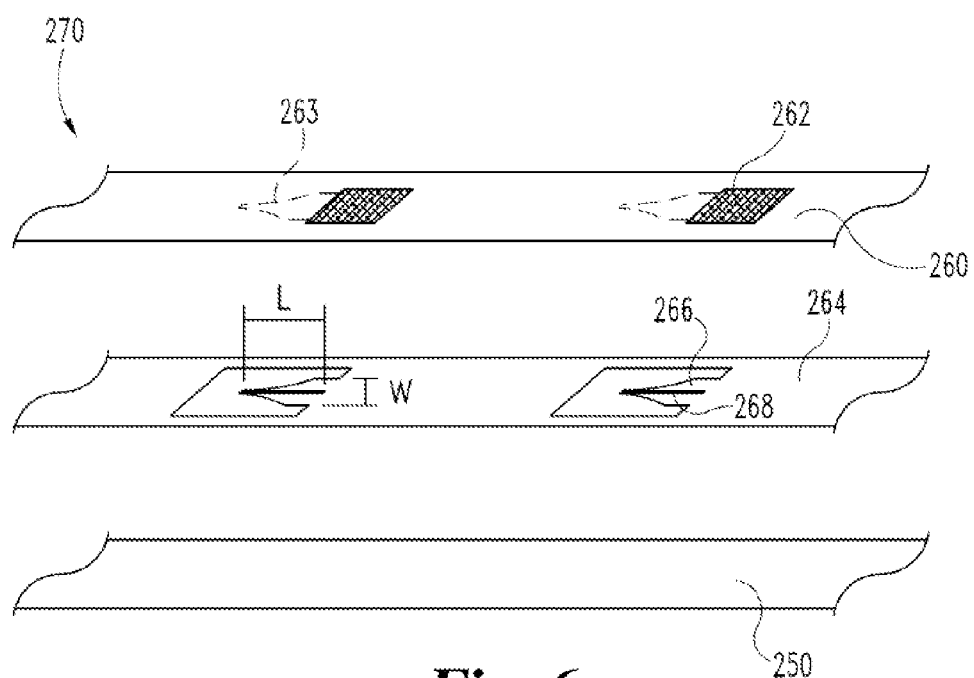
FIG. 6 is an assembly view of a tape with integrated test strips according to another embodiment.

Turning now to FIG. 6, a tape 270 configured for an integrated lancing and testing device is depicted. Tape 270 is assembled from multiple tape layers laminated or fused together, such as with heat or pressure sensitive adhesive. A lancet layer 264 is the intermediate layer and provides the lancets 266. The lancet layer 264 is formed by etching or punching the lancets 266 out of a tape stock as described above. As depicted in FIG. 6, the lancets 266 have a longitudinal capillary groove 268 that begins at or near the lancet tip and extends down the lancet length to facilitate conveying the bodily fluid down the lancet. The lancet layer 264 is mounted to a base layer 250 of tape stock, which provides additional support and structural rigidity to the finished tape 270, as needed.

A test media layer 260 carries at least one test media 262 for each of the lancets 266, and it can be formed by printing or inking the appropriate reagent(s) onto an appropriate tape stock. The test media layer 260 is then mounted onto the lancet layer 264 with the test media 262 facing the lancet layer 264 so as to sandwich the test media 262 between layers 264 and 260. The test media 262 are generally aligned with the base of the capillary grove 268 so as to receive the bodily fluid conveyed down the grove 268, as described more fully below.

Figure 7:
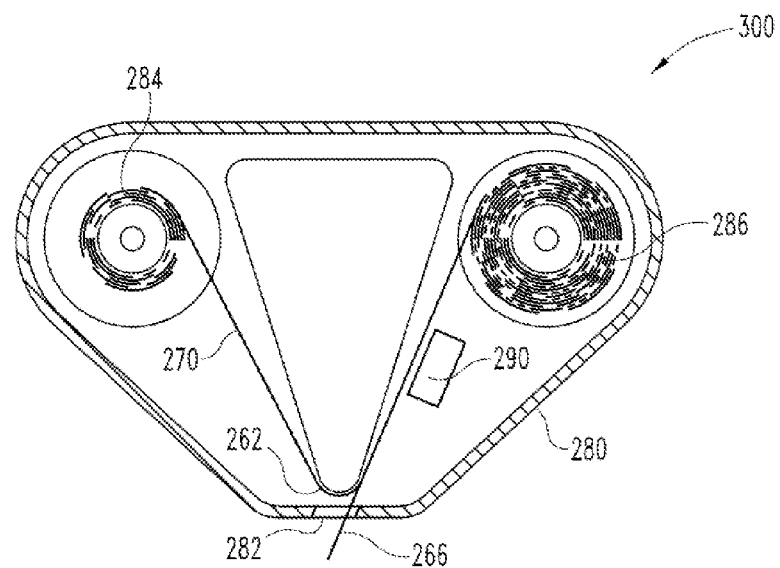
FIG. 7 is a sectional view of a multi-use lancing device employing the tape with integrated test strips of FIG. 6.

Referring now to FIG. 7, the formed tape 270 can be mounted in a housing 280 having a lancing opening 282 with the tape 270 configured for the reel to reel transfer from a supply reel 284 to a storage reel 286 as described above. The tape 270 is positioned such that the test media layer 260 is outermost, i.e. closest to sensor 290 in the FIG. 7 view. Accordingly, in this embodiment, one function of the test media layer 260 is to cover and protect the test media 262 prior to use. The test media layer 260 is also covering the tips of the lancets 266 and is designed to be punctured by a lancet 266 when the tape 270 is bent. To facilitate this puncturing, the test media layer 260 optionally includes microperforations 263, formed for example by laser cutting, generally along the outline of the lancets 266. In the illustrated embodiment, the sensor 290 is an optical sensor, and to facilitate interrogation of the test media 262, the test media layer 260 is constructed of material that passes the wavelength of interest.

During assembly of the tape 270, care is taken to assure that the lancets 266 of the lancet layer 270 are able to separate from the base layer 250 and puncture through the test media layer 260 when the tape 270 is placed around a sharp bend. Accordingly, the tape 270 is utilized to sequentially provide a lancet 266 and to activate the provided lancet 266 through the lancing opening 282 in accordance with the embodiments described above.

Once the tissue is lanced, the bodily fluid sample is captured in the capillary groove 268 of the lancet 266 and capillary forces drawn the fluid sample to the test media 262. Additional capillary forces may be provided by a flap of the test media layer 260 that is formed when the lancet 266 punches through the test media layer 260. This flap (corresponding to microperforations 263) will contact the lancet 266 after the lancing and rest against at least a portion of the capillary grove 268, providing additional wicking forces for conveying the fluid along the capillary groove 268 to the test media 262. Test media layer 260 can be constructed of a material that enhances the wicking force, for example one that is hydrophilic.

Having contacted the bodily fluid to the test media 262, the test media is next positioned by the optical sensor 290. After the appropriate time interval, the sensor 290 reads the test media 266 through the test media layer 260. An output representing at least one property of the bodily fluid may then be presented to the user on a display (not shown), such as a LCD screen.

In a variation, rather than or in addition to having the lancets 266 on the outside of the lancet layer 266 (i.e. the side facing the test media layer per the FIG. 6 view), as described above, a test media 262 may be positioned on the underside of the lancets 268, for example on the carrying tape 250 generally adjacent the lancet 266 when the lancet is not extending from the tape 270.

A still further variation involves capturing the bodily fluid directly from the tissue, i.e. without using the capillary groove 268. For such direct capture, the tissue that has been lanced and is now expressing the bodily fluid can be directly pressed against the test media 262. An appropriate place for such a test media 262 would be at a location on the uppermost surface of tape 270 (per the FIG. 6 view) that is spatially removed from the lancet 266 to avoid inadvertently touching the now contaminated lancet 266 during such direct transfer from the tissue to the tape 270.

In a further embodiment, a lancet and its associated test media are provided on the tape in the form of an integrated lancing test strip as described more fully in commonly owned U.S. application Ser. No. 10/767,522, filed Jan. 29, 2004 and titled Integrated Lancing Test Strip.

A common medical test, and one for which the present invention is particularly but not exclusively applicable, is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, the test system 300 can take advantage of an oxidation/reduction reaction which occurs using an oxidase/peroxidase detection chemistry. In this form, the test media 262 is exposed to a sample of the bodily fluid for a suitable period of time, and there is a color change if the analyte (glucose) is present. Typically, the intensity of this change is proportional to the concentration of analyte in the sample. The sensor 290 can be an optical sensor such as a reflectance spectrophotometer operating a selected wavelength, which serves to compare the color of the reagent to a known standard to determine the amount of analyte present in the sample. Electrochemical and other systems could also be employed. It is to be appreciated that, where the dry reagent chemistry employed renders it appropriate, the test media tape 263 serves to keep the underlying test media 262 sterile and substantially free from moisture prior to use.

Figure 8:
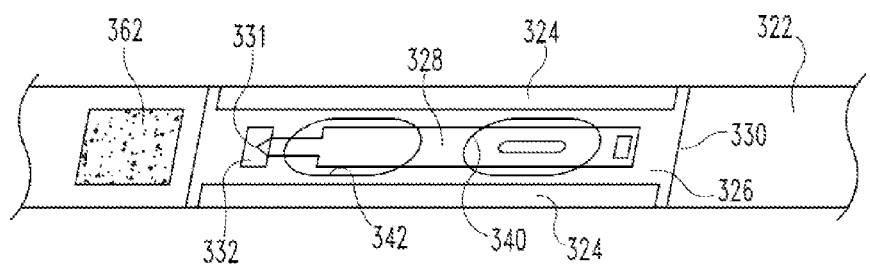
FIG. 8 is a perspective view of a tape carrying a lancet according to a further embodiment.
Figure 9:
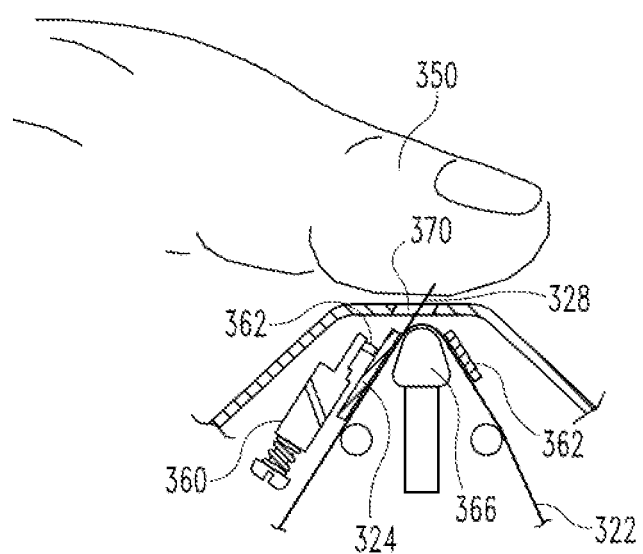
FIG. 9 is a sectional view of a multi-use lancing device employing the tape of FIG. 8.

While the embodiments illustrated in FIGS. 1-7 have involved lancets that were integral with the tape, variations of these and other embodiments are contemplated where the lancets are not integral with the tape and are activated for lancing independently from the tape. One such embodiment is depicted in FIGS. 8 and 9, wherein the lancets 238 are contained on the carrying tape 322 between a pair of raised side members 324 defining a longitudinal slot 326 along the length of the tape 322. The sharp tip 331 of the lancet 328 is initially protected under a sterile cover 332, and the entire lancet 328 is covered by a piece of retaining material 330. The material 330 is affixed to the side members 324 and covers the lancet 328 save for the portions exposed by the front and rear access openings 342 and 340 in the retaining material 330. A test media 362 is provided on the tape 322 near the lancet tip 331.

Referring now to FIG. 9, the tape 322 is supplied to position a lancet 328 adjacent a bend in the tape in the reel-to-reel manner described above, or in any other suitable manner. An activator 360 having a pin 362 then engages a corresponding slot on the lancet 328 to withdraw the lancet from the sterile cover 332 and to bring the tip 331 into the front opening 342 of the retaining material. When it is no longer constrained by the retaining material, the tip 331 of the lancet 328 is allowed to freely extend into the activating position, as depicted in FIG. 9. The activator 360 then advances and retracts the lancet 328 in the back and forth lancing motion to lance the adjacent tissue 350, depicted in this example as a fingertip. The activator 360 then releases the lancet 328, leaving it at least partially under the retaining material 326, and the tape and the used lancet 328 are advanced to storage. This advancement of the tape simultaneously positions the test media 362 adjacent the opening for direct transfer of the bodily fluid from the tissue 350 to the test media 362 and subsequent analysis by optical reader 366.

To facilitate the direct transfer of bodily fluid from the tissue 350 to the test media 362, the opening 370 can be constructed as a flexible cone that is mechanically deformed by the users finger to allow the finger to contact the test media 362. Alternatively or in addition, the optical reader 366 can be adapted to displace the tape 322 towards and/or into the opening 370 (i.e. upwardly in the FIG. 9 view) to facilitate the direct fluid transfer.

In still other forms, the sample may be collected via a capillary groove (not shown) on the lancet 328. In this embodiment the activator 360 may hold the lancet 328 while the tape 322 is advanced, and then the activator 360 may position the lancet 328 to transfer the captured bodily fluid to the test media 362. For other mechanism of collection or after the lancet is no longer needed, the activator 360 can optionally fully remove the lancet 328 from the tape 322 and move it to a discard location, or the activator 360 can replace the lancet 328 under the retaining material 330 for storage in the storage section of the tape 322.

The embodiments described herein can be incorporated into a battery powered handheld device wherein some or all of operations described herein are automated. Such an automated device could include appropriate electric motors or solenoids for advancing the tape and for cocking and/or firing the lancet, along with the appropriate controllers and user interface (such as one or more buttons) as would occur to those of skill in the art.

For example, using the FIG. 9 embodiment, one or more of the follow steps can be automated: advancing the tape to positioning a lancet into an activating position; engaging the lancet with the activator; activating the lancet to obtain the bodily fluid sample; positioning the test media adjacent the opening to receive the bodily fluid sample; contacting the bodily fluid sample to the test media (e.g. moving the optical reader); interrogating the test media with the optical reader; displaying the results; moving the used lancet and test media to storage.

In a preferred form, an entire acquisition and testing cycle is automated and is initiated by the user turning on the device, and after being prompted, pressing a button. The acquisition and testing cycle also can provide for user intervention throughout the cycle, for example to repeat a step or to stop the process altogether. For example after lancing, the automated cycle can prompt the user for another button press before continuing to test the sample. In this way, if the lancing was unsuccessful, the user can avoid wasting the test media, and the device can provide the option of re-lancing using the same lancet.

It is to be understood that many conventional lancets are generally cylindrical needles, i.e. they are circular in cross section along their longitudinal length. This type of construction generally results in a lancet of generally uniform rigidity, i.e. that resists flexing equally in all directions. It is to be understood, however, that while lancets useful in the present invention can generally take any form, advantages can be achieved when the lancets are constructed such that there is a noticeable degree of flexibility in at least one direction, such that the lancets can be flexed while in the storage position and generally linear while in the activating position. One mechanism for achieving this flexibility is to construct the lancets such that at least a portion of their length is non-circular in cross section. More specifically, the cross-section along the lengths of lancets according to certain embodiments of the invention can be substantially non-circular, and more preferably of high aspect ratio, e.g. having an aspect ratio of at least 3.

As a particular example of this high aspect ratio cross-sectional construction, the lancets illustrated herein are generally planar, or rectangular in cross section along their length. For example, the lancets 266 of FIG. 6 have a length L and a width W that are about equal, but both the length L and the width W are substantially greater than the thickness of the lancets (and of the tape). Likewise, the lancets 28 depicted in FIG. 1 are also planar, though in addition to being high aspect along their length (i.e. width to thickness ratio), lancets 28 also have a high length to width ratio. Lancets having non-planar profiles or variations on planar profiles are also contemplated, for example via the provision of reinforcing structures or other features, such as longitudinally extending ribs, to modify or enhance the structural rigidity of the lancets 28 or 266.

However, in one form, any such substantial deviations from planar are absent, at least along a substantial portion of the lancet body, i.e. at least about 25% of one major surface is substantially planar. In other forms, a major portion of the lancet body, i.e. at least about 50% is substantially planar. In other forms, planar portions make up at least 70% of at least one major surface of the lancet.

The lancets and the tape can be constructed of any suitable material or combination of materials. For example, a lancet tape can be constructed from a commercially available 316 stainless steel full hard shim stock or an other suitable thin foil constructed of metal, plastic or plastic composite. A suitable thickness for the tape stock may be between about 1 and 10 mill. Stamping, photoetching, laser cutting, and/or other methods can be employed to produce the lancets from a tape blank and to achieve sharp and/or beveled edges on the lancets and the optional capillary channel therein. Alternatively, the lancets can be formed by metal deposition onto a suitable carrier tape. In one embodiment, the lancets are created from two different materials, for example by affixing sharp metals tips to plastic lancet bodies.

CLOSURE

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. For example, while a combination lancing and testing device has been described where the test media is integrated on the same carrying tape as the lancets, the test media can be separate from the lancet carrying tape, for example configured as a cassette of test strips as described in commonly owned application Ser. No. 10/164,828, Pub. No. 2002/0188224.

Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A method for obtaining a bodily fluid sample comprising:
    providing a reel-to-reel tape carrying a plurality of lancets that are non-circular in cross section along a major portion of a length of each of the plurality of lancets, the tape having a length and defining a supply section of the tape, a storage section of the tape, and an activating section of the tape that spans between the supply and the storage sections wherein the activating section of the tape is translatable independently of the supply section of the tape and the storage section of the tape;
    advancing the tape to position a first lancet adjacent a bend in the activating section of the tape with a sharp tip of the first lancet spaced from the tape;
    translating only the activating section of the tape with a mechanism without activating the supply section and the storage section of the tape to pierce tissue with the sharp tip of the first lancet; and
    after the piercing, advancing the tape to bring the sharp tip of the first lancet closer to the tape wherein the supply section of the tape is wrapped around a supply reel and the storage section of the tape is wrapped around a storage reel, the supply reel and the storage reel being spaced apart from each other, and either the supply reel or the storage reel is configured to advance the tape.

2. The method of claim 1 further comprising:
    after the piercing, positioning a second lancet adjacent the bend in the tape with the sharp tip of the second lancet spaced from the tape; and
    translating the activating section of the tape independently of the supply section and the storage section to pierce tissue with the sharp tip of the second lancet.

3. The method of claim 1 further comprising:
    contacting a bodily fluid produced from the piercing with a test media carried by the tape.

4. The method of claim 3 wherein the bodily fluid translates along a capillary groove in the lancet to contact the test media.

5. The method of claim 1 wherein the lancets are carried on the tape with a sharp tip of each of the lancets pointing away from a direction of tape advancement.

6. A method for obtaining a bodily fluid sample comprising:
    providing a reel-to-reel tape carrying a first lancet on a service loop portion of the tape, the tape having a length and defining a supply section of the tape, a storage section of the tape, and the service loop portion of the tape that spans between the supply and the storage sections, the service loop portion of the tape is translatable independently of the supply and the storage sections;
    moving either the storage section or the supply section of the tape to position the first lancet carried by the tape adjacent a bend in the service loop portion of the tape; and
    relatively translating only the service loop portion of the tape with a mechanism without activating the remainder of the tape to lance tissue with the first lancet.

7. The method of claim 6 wherein the mechanism includes a pivoting member and the translating includes pivoting the pivoting member.

8. The method of claim 6 further comprising:
after the translating, advancing the tape to position a second lancet adjacent the bend in the service loop; and
lancing tissue with the second lancet.

9. A method for obtaining a bodily fluid sample comprising:
providing a reel-to-reel tape carrying a plurality of lancets that are non-circular in cross section along a major portion of a length of each of the plurality of lancets, the tape having a length and defining a supply section of the tape, a storage section of the tape, and the service loop portion of the tape that spans between the supply and the storage sections, the service loop portion of the tape is translatable between the supply and the storage sections; and
lancing tissue with a first lancet by relatively translating only a service loop portion of the tape with a mechanism wherein a remainder of the tape is stationary during lancing.

10. The method of claim 9 further comprising:
after lancing with the first lancet, advancing the tape; and then
lancing tissue with a second lancet by relatively translating the service loop portion of the tape.

11. The method of claim 9 further comprising:
providing a supply reel and a storage reel for carrying the tape wherein the supply reel and the storage reel remain stationary while the service loop portion of the tape translates.

12. The method of claim 1 further comprising:
providing a pair of wheels that the activating section of the tape passes over; and
moving one of the pair of wheels in a linear direction along a guiding slot to relatively translate the activating section of the tape.

13. The method of claim 1 wherein the supply section and storage section are stationary during lancing.

14. The method of claim 6 further comprising:
the mechanism includes a pair of wheels for carrying the tape; and
moving one of the wheels in a linear direction along a guiding slot to relatively translate the service loop portion of the tape.

15. The method of claim 14 wherein the supply section is wrapped around a supply reel and the storage section is wrapped around a storage reel, and the supply section and storage section are stationary during lancing.

* * * * *